United States Patent [19]

Rauber et al.

[11] Patent Number: 4,895,851
[45] Date of Patent: Jan. 23, 1990

[54] USE OF OXOQUINAZOLINE DERIVATIVES IN THE TREATMENT OF HYPERURICAEMIA

[75] Inventors: Gerhard Rauber, Ingelheim am Rhein; Roland Stechert, Bingen am Rhein, both of Fed. Rep. of Germany

[73] Assignee: Boehringer Ingelheim Zentrale GmbH, Ingelheim am Rhein, Fed. Rep. of Germany

[21] Appl. No.: 323,511

[22] Filed: Mar. 14, 1989

Related U.S. Application Data

[62] Division of Ser. No. 152,190, Feb. 4, 1988, Pat. No. 4,861,784.

[30] Foreign Application Priority Data

Feb. 11, 1987 [DE] Fed. Rep. of Germany ....... 3704203

[51] Int. Cl.$^4$ .......................................... A61K 31/505
[52] U.S. Cl. .................................................. 514/267
[58] Field of Search ........................................ 514/267

*Primary Examiner*—Stanley J. Friedman
*Attorney, Agent, or Firm*—Alan R. Stempel; Mary-Ellen M. Timbers; Frankhouser David E.

[57] ABSTRACT

Oxoquinazoline derivatives of formulae

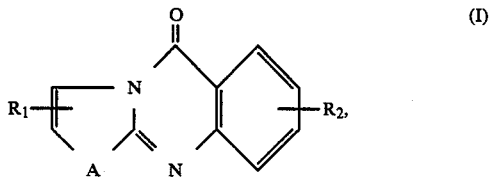

and

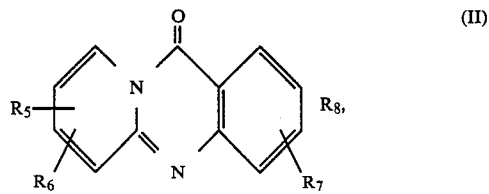

(the symbols are defined in the specification) are well-tolerated drugs for treating hyperuricaemia.

1 Claim, No Drawings

USE OF OXOQUINAZOLINE DERIVATIVES IN THE TREATMENT OF HYPERURICAEMIA

This is a division of application Ser. No. 152,190, filed Feb. 4, 1988, U.S. Pat. No. 4,861,784.

The invention relates to the use of certain known oxoquinazoline derivatives in the treatment of hyperuricaemia.

Hyperuricaemia is the pathophysiological cause of gout. The drugs currently available for the treatment of hyperuricaemia are admittedly effective but have various undesirable effects. They are either uricosurics (agents which increase the secretion of uric acid, such as probenecid, sulphine pyrazone, benzbromarone) or uricostatics (agents which inhibit the synthesis of uric acid, such as allopurinol).

The profile of side effects of these preparations is specifically as follows:
- with probenecid, 10% of patients may suffer gastro-intestinal disorders and in 4% of cases there may be allergic skin reactions and in some individual instances nephrotic syndrome (kidney disease) has also been described.
- Sulphine pyrazone simultaneously acts as a thrombocyte aggregation inhibitor and may also lead to gastro-intestinal disorders. In addition, sodium retention (leading to water retention) and in individual cases agranulocytosis (damage to the blood-forming system) are also described.
- The administration of benzbromarone may also lead to gastro-intestinal disorders.
- Apart from gastro-intestinal disorders, allopurinol may also result in undesirable effects on the blood-forming system, although these are extremely rare. Pruritus and allergies occur relatively frequently and in rare cases Lyell syndrome (scalded skin syndrome) is also described.

It has now been found that, surprisingly, the compounds according to German Offenlegungsschrift P 25 57 425 (or French Application No. 76 38 135) and European Patent Application 0 113 911 are particularly suitable for the treatment of hyperuricaemia.

The substances which may be used according to the invention are compounds of formula

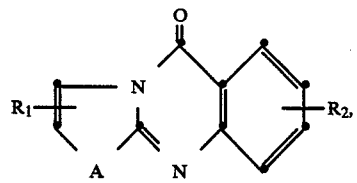

wherein
A represents one of the groups —CH=CH—, —CH=N— or S,
$R_1$ represents (a) hydrogen, a lower alkyl or alkoxy group or a condensed-on benzene ring or (b) a cyano, tetrazol-5-yl or —$COR_3$ group,
$R_2$ represents a cyano, tetrazol-5-yl or —$COR_4$ group or, if $R_1$ has one of the meanings given in (b), $R_2$ may also represent hydrogen, a lower alkyl or alkoxy group or a condensed-on benzene ring,
$R_3$ represents a lower alkoxy group, an amino, hydroxylamino or tetrazol-5-yl amino group or, if $R_2$ does not represent hydrogen, $R_3$ may also represent a hydroxy group and
$R_4$ represents a lower alkoxy group, a hydroxy, amino, hydroxylamino or tetrazol-5-ylamino group, which may occur as free compounds or as salts with acids or possibly bases, and compounds of formula

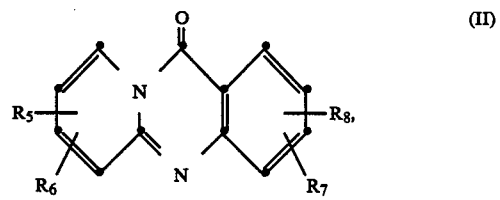

wherein either $R_5$ and $R_6$ represent hydrogen, lower alkyl, lower alkoxy or a condensed-on benzene ring and $R_7$ and $R_8$ together represent the group —N=N—NH— or $R_5$ and $R_6$ together represent the group —N=N—NH— and $R_7$ and $R_8$ represent hydrogen, lower alkyl, lower alkoxy or a condensed-on benzene ring, and the salts of these compounds with basic substances.

Compounds from German Offenlegungsschrift P 25 57 425 which are particularly worth considering for the indication according to the invention are characterised, for example, by the following formula:

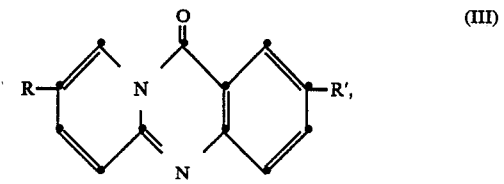

whilst the groups R and R' have the following pairs of definitions (R being mentioned first in each case):

| | |
|---|---|
| H/COOH | COOH/H |
| CH$_3$/COOH | COOH/CH$_3$ |
| OCH$_3$/COOH | COOH/OCH$_3$ |
| CH(CH$_3$)$_2$/COOH | COOH/CH(CH$_3$)$_2$ |
| H/tetrazol-5-yl | tetrazol-5-yl/H |
| H/CONH$_2$ | |
| H/CN | |

Compounds from the above-mentioned European Application which are particularly useful according to the invention are the compounds of the following formulae:

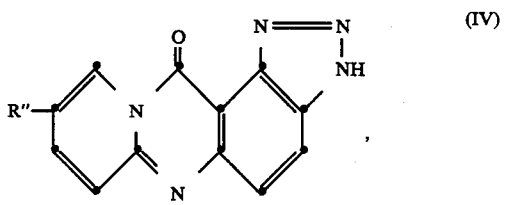

wherein R" represents H, CH$_3$, C$_2$H$_5$, CH(CH$_3$)$_2$ or OCH$_3$ and

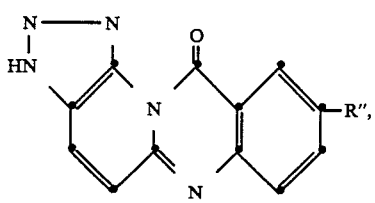 (V)

wherein R" is defined as hereinbefore.

The above-mentioned compounds have already been described as pharmaceutical compositions. The fields of application given were: the prevention and treatment of allergic diseases such as asthma, hayfever, conjunctivitis, urticaria, eczema and dermatitis. Their muscle-relaxant (bronchodilatory) and vasodilatory activity have also been mentioned.

There is no reference to any uric acid-reducing activity, nor is such an effect made obvious by the known effects.

Compared with the known agents for treating hyperuricaemia or gout, the compounds which may be used according to the invention, for example 11-oxo-11-H-pyrido[2,1-b]quinazolin-2-carboxylic acid and the salts thereof, have the advantage of being better tolerated. Thus, when more than 1000 patients were treated with this compound for a different type of indication, no side effects specific to the preparation were discovered.

For use, the compounds are processed in the usual way to form conventional galenic preparations. The primary form of administration is by oral route, preferably in capsule form; however, all other oral forms may be considered, e.g. tablets, coated tablet, granules, suspensions or delayed release forms.

The daily dosage is about 100 to 1000 mg; it may be given in 1–3 single doses.

In a study carried out on 12 ambulant patients with symptom-free hyperuricaemia, the patients were treated with 11-oxo-11-H-pyrido[2,1-b]quinazolin-2-carboxylic acid in the form of tablets containing the usual excipients. The dosage was 200 mg 3 times a day for 2 weeks with a subsequent wash-out phase lasting 1 week. Before the treatment the uric acid levels in the serum were on average $8.56 \pm 0.6$ mg/100 ml. After two weeks' treatment these levels fell significantly by 29% to $6.1 \pm 0.8$ mg/100 ml. After the washout phase they rose again to 7.7 mg$\pm 0.9$ mg/100 ml.

In another study, 8 stationary test subjects were fed with a purine-rich diet for 8 days continuously. This produced a higher level of uric acid in the serum, which was stable from the third day onwards. From the 5th day onwards the test subjects were additionally given $3 \times 200$ mg per day of the above-mentioned compound in tablet form. On the 4th day on the diet the uric acid levels had stabilised at $7.9 \pm 0.95$ mg/100 ml at a raised level. After the end of the treatment (4 days), i.e. at the end of the 8th day of the trial, the levels had fallen significantly by 35% to $5.1 \pm 0.82$ mg/100 ml. Once again, the compound was found to have a significant lowering effect on uric acid.

EXAMPLES OF FORMULATIONS

1. Tablets

| | |
|---|---|
| 11-Oxo-11-H—pyrido[2,1-b]-quinazolin-2-carboxylic acid | 100 g |
| Colloidal silica | 10 g |
| Lactose | 118 g |
| Potato starch | 60 g |
| Polyvinylpyrrolidone | 6 g |
| Sodium cellulose glycolate | 4 g |
| Magnesium stearate | 2 g |

The ingredients are processed in the usual way to form tablets weighing 300 mg.

2. Capsules

| | |
|---|---|
| Active substance of formula I or II | 300 g |
| Corn starch | 100 g |

The ingredients are thoroughly mixed and the mixture is transferred in batches of 400 mg into oblong gelatin capsules.

What is claimed is:

1. A method for treating hyperuricaemia or a disease state caused thereby, which method comprises orally administering to a host suffering from hyperuricaemia or a disease state caused thereby, a therapeutic amount of a compound of formula

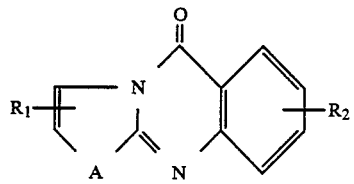

wherein

A represents —CH═CH $R_1$ represents (a) hydrogen, a lower alkly or alkoxy group or a condensed-on benzene ring or (b) a cyano, tetrazol-5-yl or —$COR_3$ group, $R_2$ represents a cyano, tetrazol-5-yl or —$COR_4$ group or, if $R_1$ has one of the meanings given in (b), $R_2$ may also represent hydrogen, a lower alkyl or alkoxy group or a condensed-on benzene ring, $R_3$ represents a lower alkoxy group, an amino, hydroxylamino or tetrazol-5-yl amino group or, if $R_2$ does not represent hydrogen, $R_3$ may also represent a hydroxy group and $R_4$ represents a lower alkoxy group, a hydroxy, amino, hydroxylamino or tetrazol-5-yl amino group, or a pharmaceutically acceptable salt thereof.

* * * * *